(12) United States Patent
Jiang et al.

(10) Patent No.: US 7,959,864 B2
(45) Date of Patent: Jun. 14, 2011

(54) DOWNHOLE SPECTROSCOPIC HYDROGEN SULFIDE DETECTION

(75) Inventors: Li Jiang, Newton, MA (US); Oliver C. Mullins, Ridgefield, CT (US); Gale H. Gustavson, Brookfield, CT (US); Christopher Harrison, Auburndale, MA (US); Bhavani Raghuraman, Wilton, CT (US); Ronald E. G. Van Hal, Watertown, MA (US); Jimmy Lawrence, Cambridge, MA (US); Kosta Ladavac, Somerville, MA (US); A. Ballard Andrews, Wilton, CT (US); Timothy Gareth John Jones, Cottenham (GB); Rogerio Tadeu Ramos, Eastleigh (GB)

(73) Assignee: Schlumberger Technology Corporation, Cambridge, MA (US)

(*) Notice: Subject to any disclaimer, the term of this patent is extended or adjusted under 35 U.S.C. 154(b) by 447 days.

(21) Appl. No.: 11/925,219

(22) Filed: Oct. 26, 2007

(65) Prior Publication Data

US 2009/0107667 A1 Apr. 30, 2009

(51) Int. Cl.
*G01N 33/24* (2006.01)
(52) U.S. Cl. .......... 422/68.1; 436/121; 436/164; 436/25
(58) Field of Classification Search .................. 436/121, 436/2
See application file for complete search history.

(56) References Cited

U.S. PATENT DOCUMENTS

| 4,252,655 A | 2/1981 | Carney |
| 4,732,213 A * | 3/1988 | Bennett et al. ............... 166/292 |
| 5,397,708 A | 3/1995 | Lessard et al. |
| 5,517,024 A | 5/1996 | Mullins et al. |
| 5,939,717 A | 8/1999 | Mullins |
| 6,223,822 B1 | 5/2001 | Jones |
| 6,758,090 B2 | 7/2004 | Bostrom et al. |
| 6,939,717 B2 * | 9/2005 | Jiang et al. .................... 436/121 |
| 6,988,547 B2 | 1/2006 | Goodwin et al. |
| 2004/0129874 A1 * | 7/2004 | Torgersen et al. ............ 250/255 |

FOREIGN PATENT DOCUMENTS

| JP | 61099849 A | 5/1986 |
| JP | 3221142 A | 9/1991 |
| JP | 05004021 A | 1/1993 |
| WO | WO95/24962 A | 9/1995 |

(Continued)

OTHER PUBLICATIONS

Henglein, A. "Photochemistry of colodial cadmium sulfate. 2. Effects of adsorbed methyl viologen and of collodial platinum." Journal of Physical Chemistry (1982) 86 p. 2291-2293.*

(Continued)

*Primary Examiner* — Yelena G Gakh
*Assistant Examiner* — Christopher A Hixson
(74) *Attorney, Agent, or Firm* — James McAleenan; Helene Raybaud; Brigid Laffey (57) ABSTRACT

Methods and related apparatuses and mixtures are described for detecting hydrogen sulfide in a formation fluid downhole. A detection mixture is combined with the formation fluid downhole. The detection mixture includes metal ions for reacting with hydrogen sulfide forming a metal sulfide, and charged nanoparticles sized so as to inhibit significant aggregation of the metal sulfide so as to enable spectroscopic detection of the metal sulfide downhole. The combined mixture and formation fluid is then spectroscopically interrogated so as to detect the presence of the metal sulfide thereby indicating the presence of hydrogen sulfide in the formation fluid. The mixture also includes chelating ligands for sustaining thermal endurance of the mixture under downhole conditions.

7 Claims, 10 Drawing Sheets

FOREIGN PATENT DOCUMENTS

| WO | 99/00575 A2 | 1/1999 |
| WO | WO01/09039 A1 | 2/2001 |
| WO | WO01/63094 A1 | 8/2001 |
| WO | WO2005/039656 A1 | 5/2005 |

OTHER PUBLICATIONS

Auvray, X., et al. "Formamide, a water substitute XIV (1) waterless microemulsions 8. Structural analysis by X-ray scattering of CTAB aggregates in formamide and in the microemulsion system (formamide, CTAB, isooctane, 1-butanol)." Colloid and Polymer Science (1987) 265 p. 925-932.*

ScienceLab.com "Material Safety Data Sheet, Formamide MSDS." Last updated Nov. 2008. [http://www.sciencelab.com/xMSDS-Formamide-9927348], accessed on Jan. 11, 2010.*

Dezelic, Gj. et al. "Electron Microscopy of Ludox Collodial Silica." Colloid and Polymer Science (1960) 171 42-45.*

Wardencki, W., Problems with the determination of environmental sulphur compounds by gas chromatography, Journal of Chromatography A, 1998, 793, pp. 1-19.

LUDOX® Colloidal Silica, Properties, Uses, Storage, and Handling, Product Information, Grace Davison, 2000, pp. 1-19.

Spaziani et al., On-line Determination of Sulfide by the 'Methylene Blue Method' With Diode-laser-based Fluorescence Detection, Analyst, Dec. 1997, vol. 122, pp. 1555-1558.

Smits et al., In-Situ Optical Fluid Analysis as an Aid to Wireline Formation Sampling, SPE Formation Evaluation, Jun. 1995, pp. 91-98.

Cardoso et al., Fluorometric fiber optic drop sensor for atmospheric hydrogen sulfide, Talanta, 1997, vol. 44, pp. 1099-1106.

Eroglu, et al., Hydrogen sulfide determination by solid surface luminescence, Fresenius J. Anal. Chem, 1996, vol. 355, pp. 667-671.

Henglein, A., Photo-Degradation and Fluorescence of Collodial-Cadmium Sulfide in Aqueous Solution, Ber. Bunsenges. Phys. Chem. 86, pp. 301-305, 1982.

* cited by examiner

| Ligand | Pb/L Thermal Endurance (150C, 24hrs O.D. Yield) | | |
|---|---|---|---|
| | 815nm | 680nm | 570nm |
| NTA (1N, 3C)  | 100% 100% 97% 95% 84% | 100% 100% 99% 93% 77% | 100% (2 hrs) 100%(17hrs) 100%(24hrs) 91% (48hrs) 72% (504hrs) |
| CA (0N, 3C)  | 68% | 69% | 71% |
| EDDA (2N, 2C)  | 68% | 65% | 68% |
| IDAA (1N, 2C)  | 48% | 39% | 38% |
| PDCA (1N, 2C, 1A)  | 66% | 71% | 83% |
| IDMPA (1N, 2P)  | ~100% | ~100% | ~100% |

DOWNHOLE SPECTROSCOPIC HYDROGEN SULFIDE DETECTION

BACKGROUND OF THE INVENTION

1. Field of the Invention

The invention is generally related to detection and sensing of properties of downhole fluids. More particularly, this patent specification relates to downhole spectroscopic detection of substances such as Hydrogen Sulfide using colloidal detection mixtures.

2. Background of the Invention

Hydrogen sulfide ($H_2S$) occurs extensively in a number of subsurface hydrocarbon reservoirs under anaerobic conditions. The presence of hydrogen sulfide is highly corrosive to casing, tubing, and other metallic and polymeric tools, an effect that is considerably accelerated by low pH and the presence of carbon dioxide. This has a significant impact on the overall hydrocarbon recovery processes, during which materials selection and corrosion control are of great importance. Additionally, $H_2S$ is hazardous to humans even at minute concentration levels (for example, about 100 ppm).

The $H_2S$ content of reservoir fluids can be determined from samples collected by wireline fluid Sampling tools such as Schlumberger's Modular Dynamics Tester or other sampling tools. Fluid samples are usually collected in metal containers, which are able to maintain the pressures at which the samples were collected. However, a problem associated with sampling fluids containing hydrogen sulfide is partial loss of the gas by reaction of the metal components, particularly those made from iron-based metals. The hydrogen sulfide gas readily forms non-volatile and insoluble metal sulfides by reaction with many metals and metal oxides, and analysis of the fluid samples can therefore give an underestimate of the true sulfide content.

As a result, the in situ detection and measurement of hydrogen sulfide is widely regarded as a critical parameter needed for well completion and production strategies. Due to the high chemical reactivity of sulfide species, various detection strategies including spectroscopy, electrochemistry, chromatography and combinations thereof have been proposed. For example, see Wardencki, W. J. "Problems with the determination of environmental sulphur compounds by gas chromatography" Journal of Chromatography A, Vol 793, 1 (1998). U.S. Pat. No. 6,939,717B2 describes feasible electrochemical and optical methodologies and embodiments aimed at downhole detection of hydrogen sulfide.

SUMMARY OF THE INVENTION

The present invention relates to a mixture that is provided for use in downhole spectroscopic detection of hydrogen sulfide. The mixture includes metal particles for reacting with hydrogen sulfide thereby forming a metal sulfide species and nanoparticles sized so as to inhibit significant aggregation of insoluble metal sulfide species so as to enable spectroscopic detection of the metal sulfide species downhole. Chelating ligands are preferably included in the mixture for sustaining thermal endurance of the mixture under downhole conditions. The metal particles are preferably metal ions.

In accordance with another embodiment of the invention, a method of detecting hydrogen sulfide in a formation fluid downhole is also provided. A detection mixture is combined with the formation fluid downhole. The detection mixture includes metal particles for reacting with hydrogen sulfide forming a metal sulfide, and nanoparticles sized so as to inhibit significant aggregation of the metal sulfide so as to enable spectroscopic detection of the metal sulfide downhole. The combined mixture and formation fluid is then spectroscopically interrogating so as to detect the presence of the metal sulfide thereby indicating the presence and/or quantity of hydrogen sulfide in the formation fluid.

In accordance with another embodiment of the invention, a system is provided for detecting hydrogen sulfide downhole. The system includes a detection mixture for reacting with hydrogen sulfide, a downhole mixture delivery system for exposing the detection mixture to fluids collected from a subterranean formation in a downhole setting, and an optical detection system for detecting the reacted mixture that indicated the presence of hydrogen sulfide in the exposed formation fluid.

In accordance with another embodiment of the invention, a method is also provided for dispersing a compound which is otherwise insoluble in a solvent into a homogeneous solution for use spectroscopic analysis of a fluid comprising the step of combining the compound with the solvent and nanoparticles, wherein the nanoparticles are sized and charged so as to inhibit significant aggregation which would otherwise hinder spectroscopic analysis of the fluid.

Further features and advantages of the invention will become more readily apparent from the following detailed description when taken in conjunction with the accompanying Drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

The present invention is directed to a mixture that is provided for use in downhole spectroscopic detection of hydrogen sulfide. The mixture includes metal particles for reacting with hydrogen sulfide thereby forming a metal sulfide species and nanoparticles sized so as to inhibit significant aggregation of insoluble metal sulfide species so as to enable spectroscopic detection of the metal sulfide species downhole. Chelating ligands are preferably included in the mixture for sustaining thermal endurance of the mixture under downhole conditions. The metal particles are preferably metal ions.

It has been found that a difficulty in prior Hydrogen sulfide ($H_2S$) detection methods exist due to rapid precipitation when the $H_2S$ reacts with the metallic or other substances used for detection. Since the metal sulfide very quickly precipitates out of the detection solution, its optical detection is often very difficult or impractical. According to embodiments of the invention, mixtures can be provided that have a relatively large surface area onto which the reacting sulfide can precipitate. The surface area is provided in the form of particles that are small enough that when optical detection methods can be used, such as with visible light, the precipitated sulfide has the appearance of being a fully solvated, although on a molecular level the sulfide is no longer in the solution phase.

According to embodiments of the invention, a specific detection and measurement strategy for hydrogen sulfide can be provided based on the colorimetric features of metal sulfide species that are dispersed into a homogeneous colloidal dispersion in the presence of an overwhelming amount of silica nanoparticles in an alkaline aqueous medium. For example, a ratio of Si 7000 mM:$Pb^{2+}$ 3 mM has been found to be effective in some applications. By adding an appropriate chelating ligand, the metal-ligand-silica system sustains high recovery yield after extensive thermal treatment that is representative of downhole sampling and detecting processes. The provided mixture can be used in combination with a downhole optical detection system, such as Schlumberger's Live Fluid Analyser (LFA), which is operated as part of Schlumberger's openhole logging tool Modular Formation Dynamics Tester (MDT). Accordingly, a viable means for in situ detection and measurement of hydrogen sulfide in the formation gas can be provided.

Figure 1:
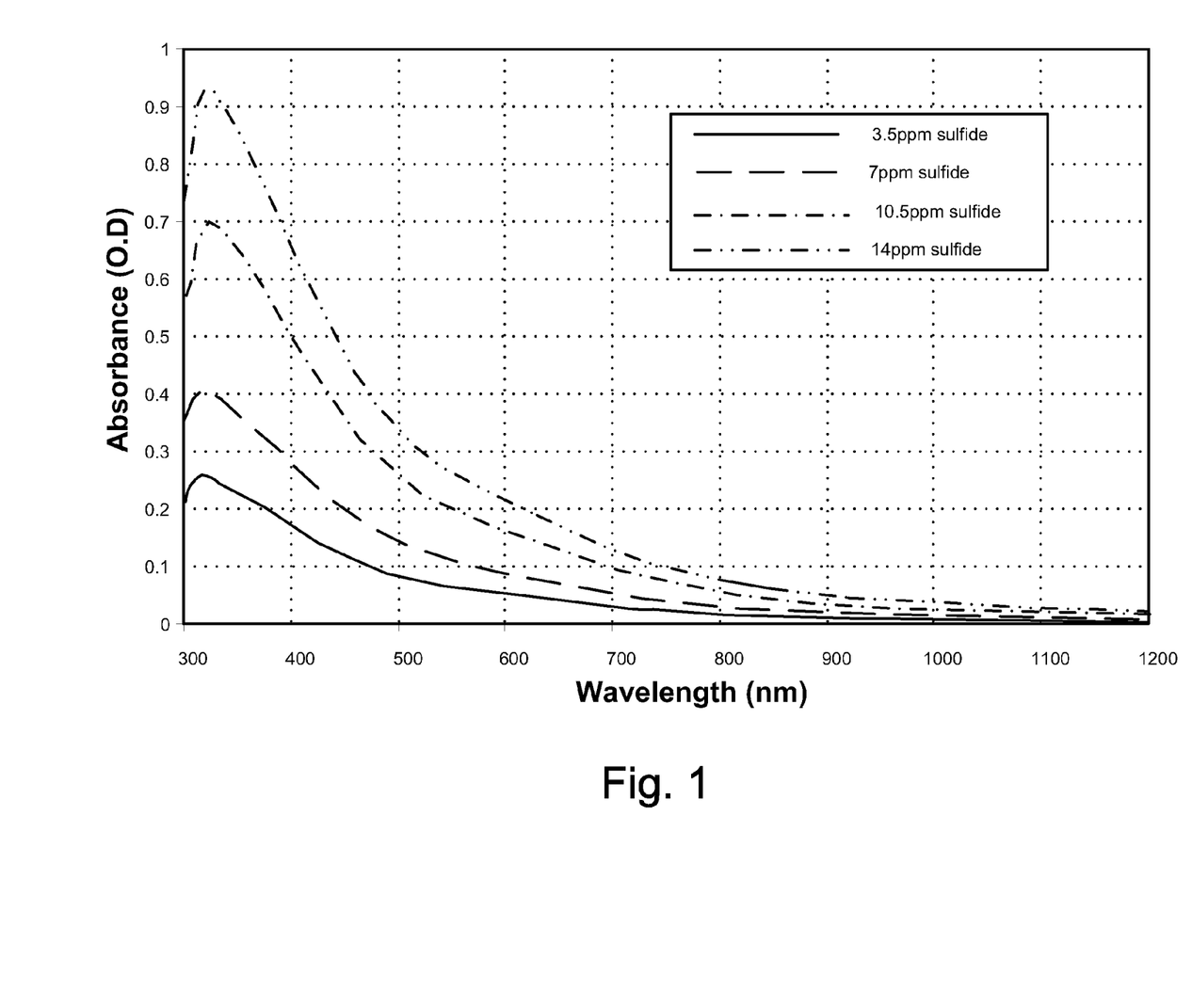
FIG. 1 shows a set of typical visible spectra of a homogeneous colloidal dispersion according to embodiments of the invention.

FIG. 1 shows a set of typical visible spectra of a homogeneous colloidal dispersion according to embodiments of the invention. In this example, a mixture comprising of $Pb^{2+}$/NTA-Ludox® and water reacted with increasingly higher concentrations of sulfide. In general, the curves exhibit a shoulder at around 600 nm and a peak at around 310 nm. FIG. 1 shows that the sensitivity of the solution is sufficient to detect sulfide concentrations as low as around 3 ppm. Additionally, the proportional growth of the optical density with the sulfide concentration can be used to make quantitative measurements.

The water insoluble metal sulfide should be dispersed into homogeneously distributed particles that are small enough to remain in the bulk of the solution. This is preferably achieved via charge matching between the metal species and the silica particles (4). Colloidal particles that have been found to be suitable for some applications are marketed under the brand name Ludox®, and can be obtained from either GRACE Davison or Sigma-Aldrich. The Ludox® particles are discrete uniform spheres with a diameter of about 22 nm. They have no internal surface area or apparent crystallinity, with an apparent surface area of 150 $m^2/g$. At a typical pH of 9, the silica particle surface is negatively charged due to deprotonation of its surface silano groups. These particles (for example in a solution of approximately $3.3 \times 10^{16}$ particles/g) repel one another thereby yielding a stable solution, capable of confining the positively charged metal species either in the close proximity of, or directly onto, their surface. Such an effect has been found to be strong enough to prevent the following two adverse processes from happening: (1) precipitation of an otherwise poorly soluble metal hydroxide; and (2) precipitation/aggregation of an otherwise poorly soluble metal sulfide species into micron sized powder. This allows quantitative analysis of sulfide using absorption spectroscopy without interference from scattering. In general, it has been found the nanoparticles should be sized between about 7 nm and 25 nm. If the nanoparticles are too small, then the limit of a colloidal particle will be reached. The particles will become fully solvated in water which will result in the charge of the particles not functioning as desired. If the particles are too large, it has been found that the aqueous solution becomes overly milky or opaque so as to impede spectroscopic analysis.

Figure 2:
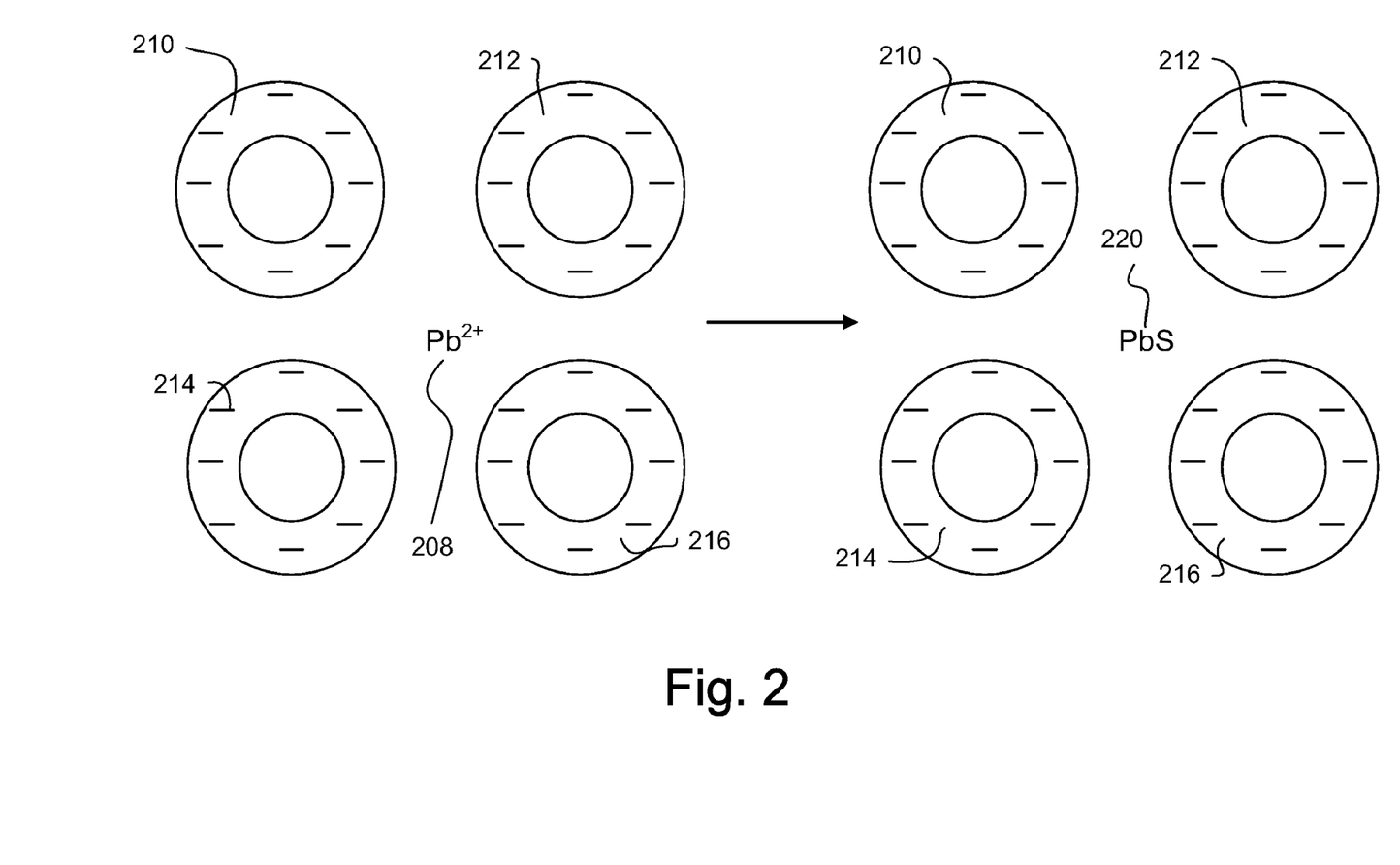
FIG. 2 illustrates a representation of lead species being confined in close proximity, or directly on to the surface of silica nanoparticles, according to embodiments of the invention.

FIG. 2 illustrates a representation of lead species being confined in close proximity, or directly on to the surface of silica nanoparticles, according to embodiments of the invention. On the left side of FIG. 2, lead ion 208 is in close proximity to silica nano particles 210, 212, 214 and 216. On the right sides of FIG. 2, lead sulfide 220 is shown in close proximity to silica nanoparticles 210, 212, 214 and 216. The confinement of the lead species by the silica nanoparticles could be a nanocage function or similar to a nanocage as shown in FIG. 2. However, the arrangement and functioning on the molecular level may not be precisely understood at present.

In selecting a suitable mixture, the thermal endurance of the reaction system should be considered in a temperature regime analogous to the anticipated wellbore conditions. For many applications, a temperature of 150° C. is suitable and is used throughout this description unless otherwise indicated. It was observed that a 24-hour baking of the $Pb^{2+}$-Ludox® binary mixture resulted in a considerably lower yield of optical density as compared to the ambient temperature counterpart. At the end of the baking period, the sample was cooled down to ambient temperature. According to an aspect of the of the invention, an appropriate chelating ligands to be selected tends to shield $Pb^{2+}$. A particularly effective ligand, nitrilotriacetic acid (NTA), was identified that consistently has the recovery yield in optical density better than 90% after 24 hour baking at 150° C.

Figure 3:
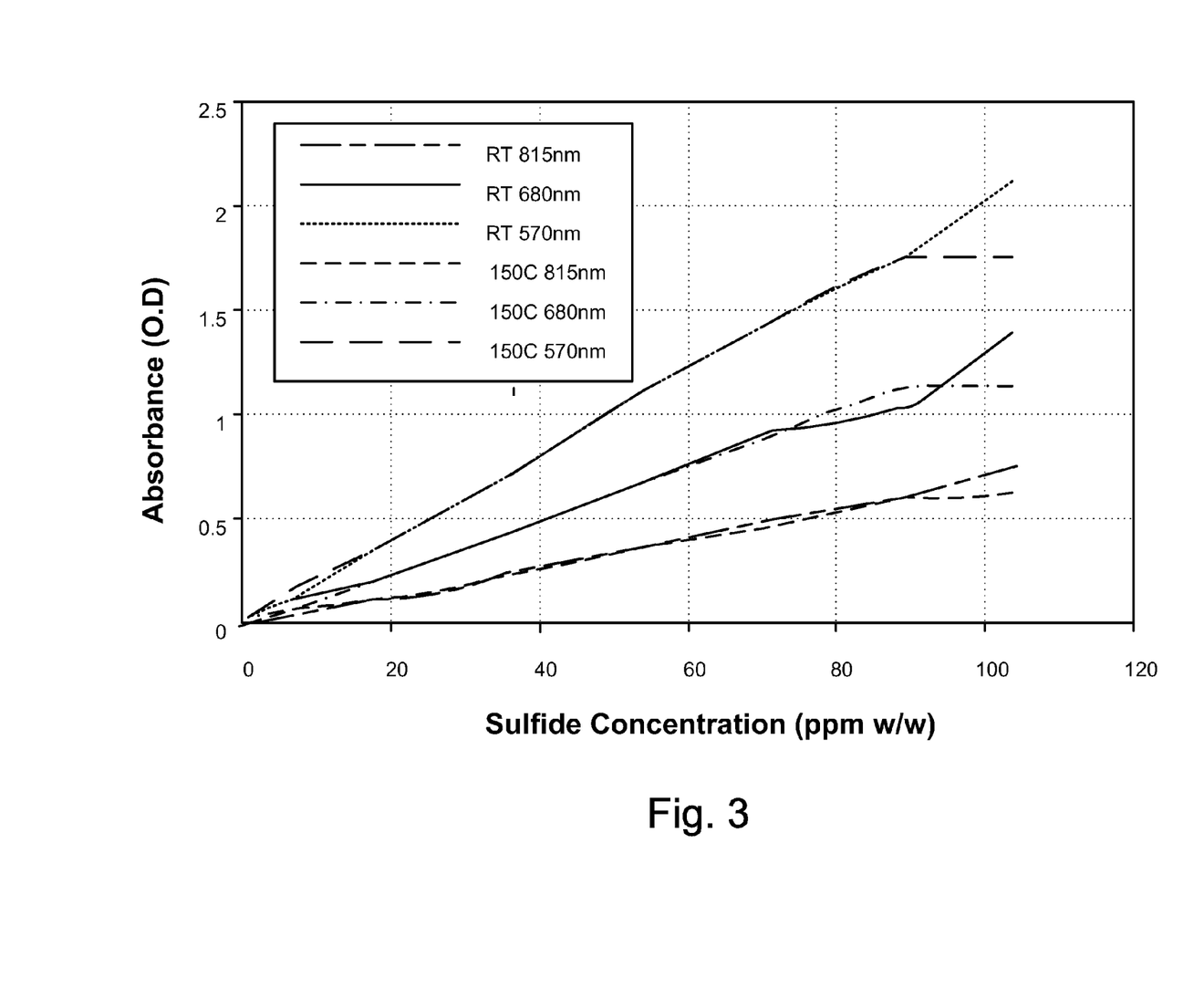
FIG. 3 shows the average values of three independent samples baked at 150° C. for 24 hours against respective ambient temperature references according to embodiments of the invention.

FIG. 3 shows the average values of three independent samples baked at 150° C. for 24 hours against respective ambient temperature references. FIG. 3 shows the absorbance versus sulfide concentration relationship at three discrete wavelengths of 815 nm, 680 nm and 570 nm. Each pair compares the ambient temperature sample to its counterpart through baking at 150° C. for 24 hours, and then probed at ambient temperature. For example, the mixture tested had the following characteristics: $Pb(NO_3)_2$ 4.03 mM, NTA 6.14 mM, Ludox® 35%, pH 9. FIG. 3 shows that the samples exhibit a nearly 100% recovery yield in optical density in all the three wavelengths at sulfide concentrations up to 89 ppm (with exception for 680 nm at this point). This concentration of sulfide approaches the stoichiometric ratio of unity with lead (theoretical threshold at 103 ppm sulfide). For sulfide concentrations in excess of those of lead ion the optical density is constant, indicating that saturation of the measurement has been reached.

In general, the pH of the mixture should be carefully selected. If the pH is too low, for example below 7.5, problems can occurs such as gelling of the Ludox® and/or multiple species of $H_2S$ occurring and the measurement may lose quantification. If the pH is too high, for example above 10.5, the silica particles will start to dissolve in the aqueous solution. Additionally, corrosion of the downhole tool and casing become a problem at high pH levels. It has been found that for many applications a pH range of 9.0-9.5 can be ideal.

Figure 4:
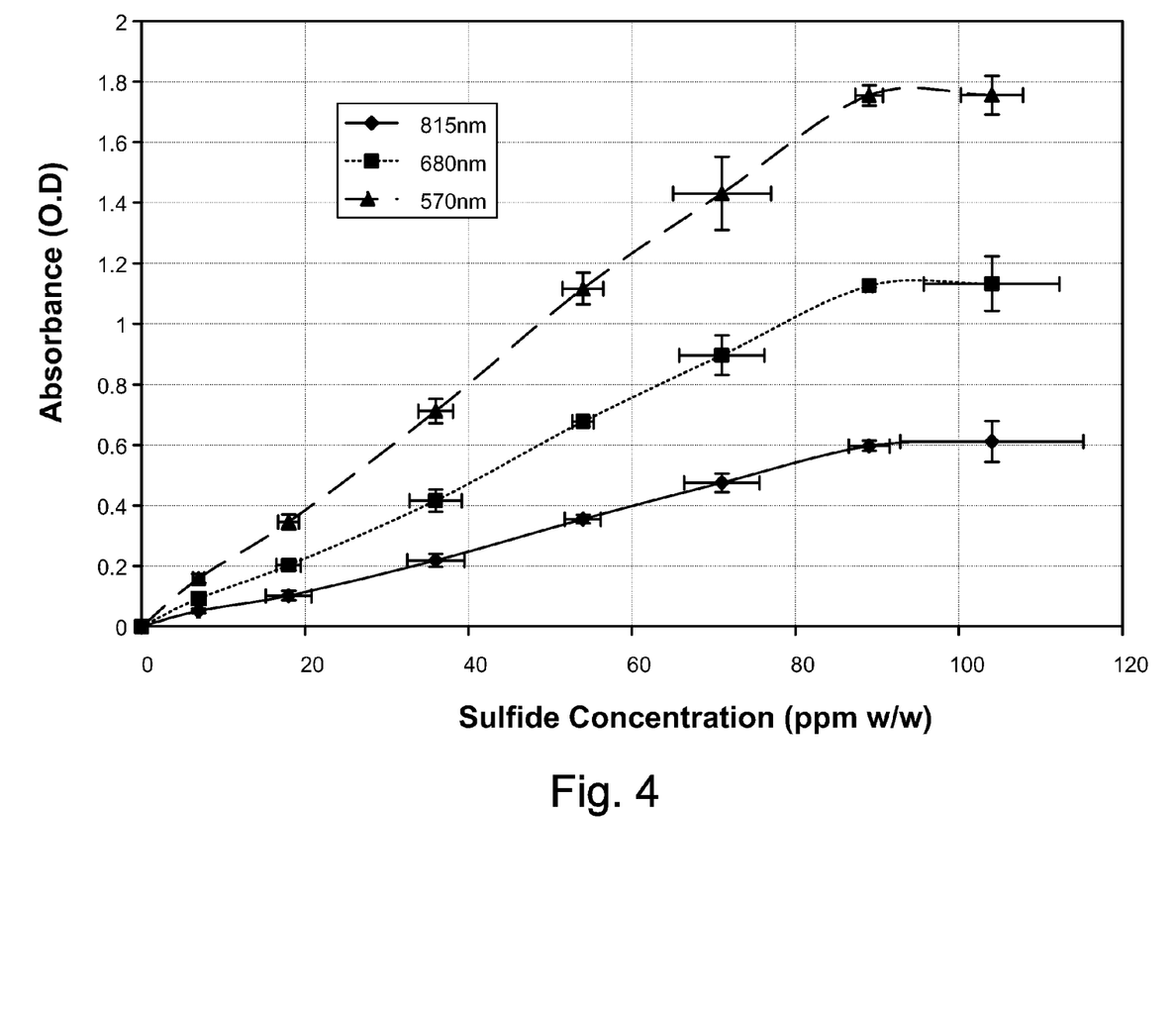
FIG. 4 shows the uncertainty of the data set is presented in FIG. 3.

Referring to FIG. 4, it has been found in general, that shorter wavelengths offer higher confidence in data accuracy. FIG. 4 shows the uncertainty of the data set is presented in FIG. 3. For example, at 570 nm, the largest uncertainty at the 7 ppm level, which is 9.6% representing a possible error of ±0.67 ppm. While the smallest uncertainty is at the 89 ppm level, which is 1.9% representing a possible error of ±1.7 ppm. These levels have been found to be well within tolerance of many intended applications.

Figure 5:
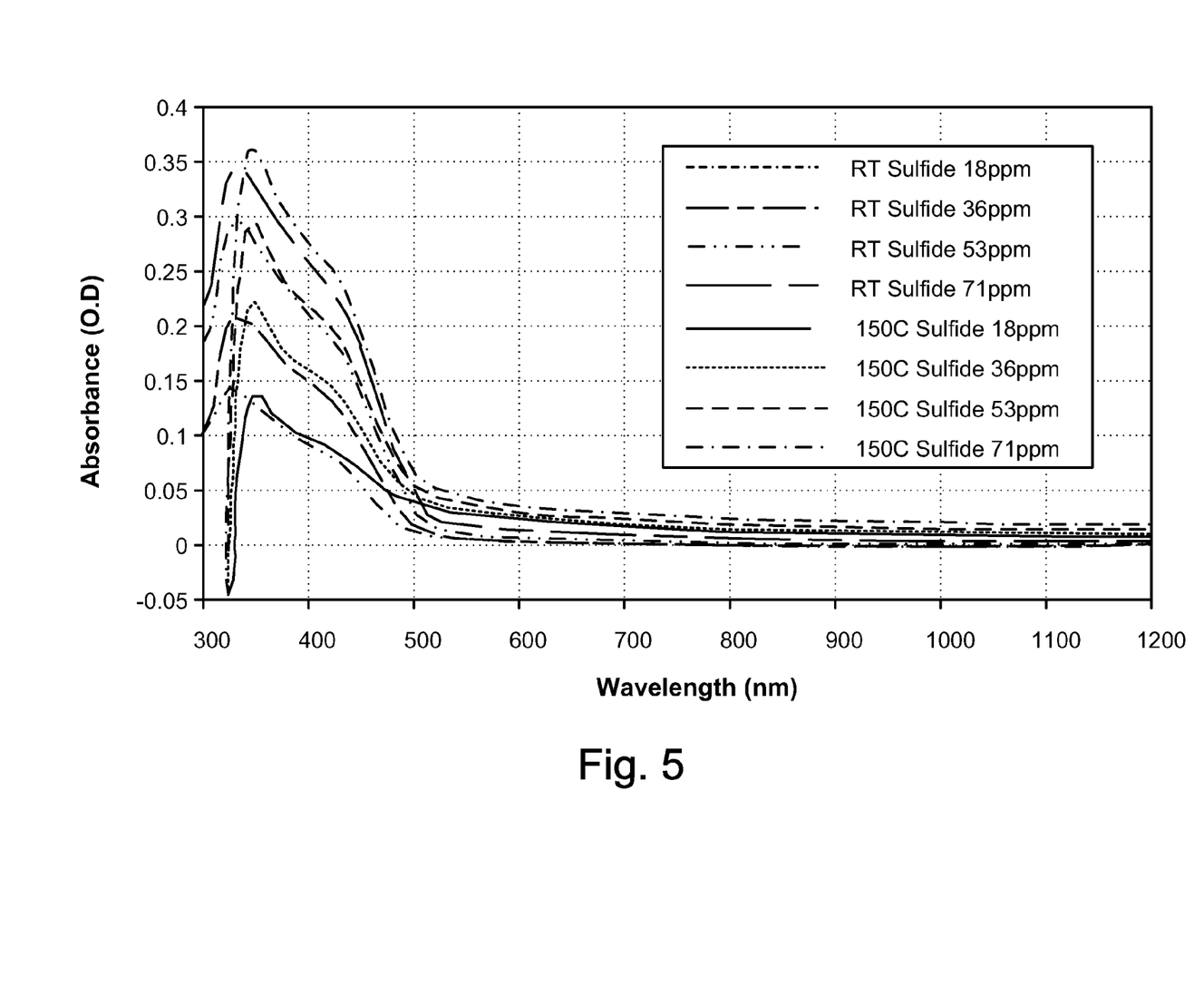
FIG. 5 shows four pairs of spectra of a Cd/NTA-Ludox® dispersion before and after baking at 150° C. for 24 hours, according to an embodiment of the invention.

FIG. 5 shows four pairs of spectra of a Cd/NTA-Ludox® mixture before and after baking at 150° C. for 24 hours, according to an embodiment of the invention. For example, the mixture characteristics were: $Cd(NO_3)_2$ 2.5 mM, NTA 5.1 mM, Ludox® 32%, pH 9. These spectra exhibit a shoulder at around 430 nm, and a peak at 315 nm that red-shift to ~350 nm as a result of baking. This cadmium system also affords high recovery yield in optical density across the sulfide concentration range from 18 to 71 ppm, representing a viable alternative to lead.

Figure 6:
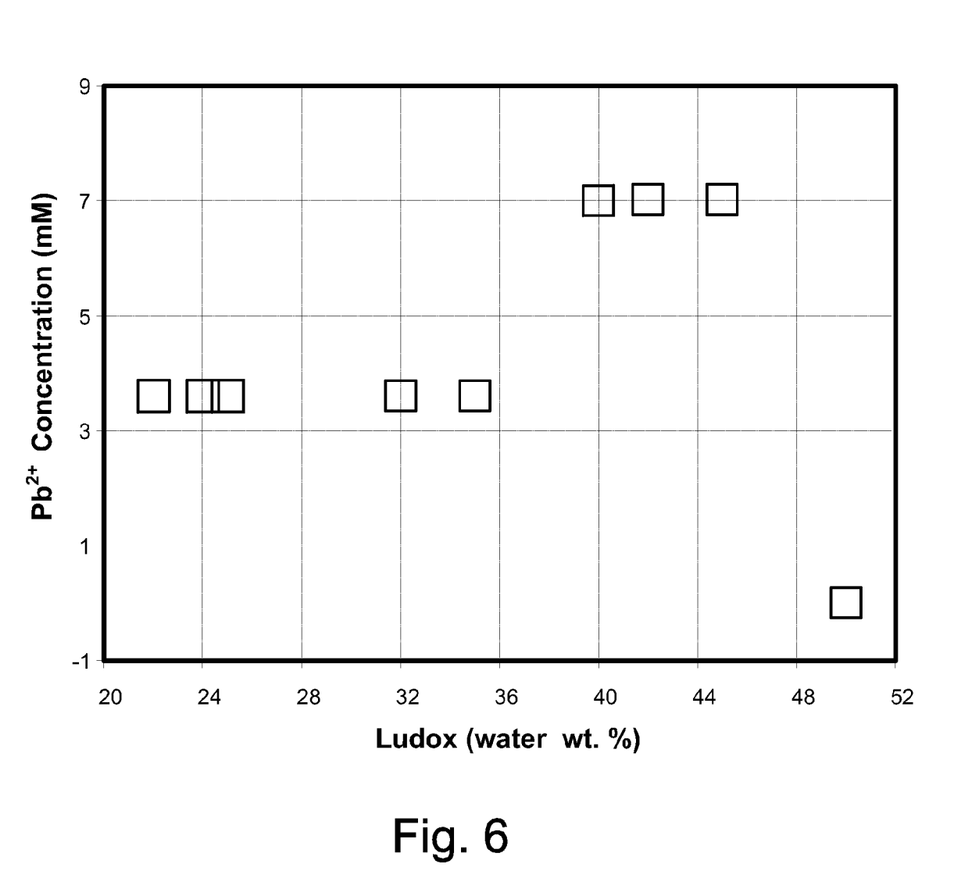
FIG. 6 shows critical loading ratios of mixtures according to embodiments of the invention.

Referring to FIG. 6, according to an aspect of the invention, it is preferable not to exceed a critical loading ratio of a particular mixture. The critical loading ratio can be defined herein as the amount (in mM) of metal ions which can be combined with a particular nanoparticle-water weight ratio, beyond which there is a significant risk of a large scale precipitation that destroys the homogeneity of the mixture. FIG. 6 shows critical loading ratios of mixtures according to embodiments of the invention. FIG. 6 shows three domains for aqueous mixtures of $Pb^{2+}$/NTA in Ludox® all after baking at 150° C. for 24 hours: (1) below 25%, the Ludox® is not sufficient to accommodate the normal amount of $Pb^{2+}$/NTA; (2) between 32-45%, the Ludox® is functioning fine with [$Pb^{2+}$] up to 7 mM; and (3) at even higher concentrations, the Ludox® tends to gel as a result of baking. Thus, after being baked at 150° C. for 24 hours, a Ludox® concentration greater than 45% makes the mixture liable to gel formation. On the other hand, at Ludox® concentrations lower than 20%, its binding capacity is not strong enough to accommodate the given amount of $Pb^{2+}$/NTA.

Figure 7:
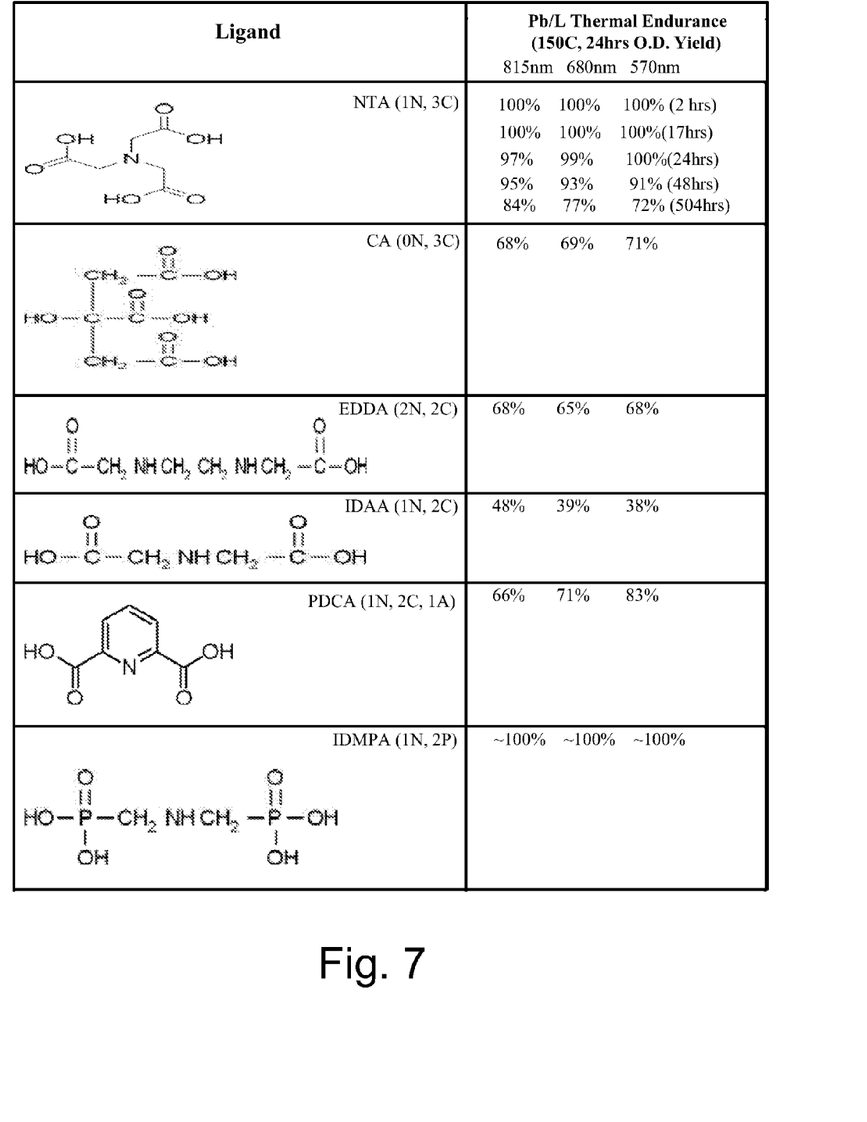
FIG. 7 is a table summarizing the results of thermal endurance test of lead coupled with a group of chelating ligands with different binding capacities, according to embodiments of the invention.

FIG. 7 is a table summarizing the results of thermal endurance test of lead coupled with a group of chelating ligands with different binding capacities, according to embodiments of the invention. The following abbreviations are used in FIG. 7: NTA—nitrilotriacetic acid, CA—citric acid; EDDA—ethylenediamine diacetic acid; IDAA—iminodiacetic acid; PDCA—pyridinediacetic acid; IDMPA—iminodimethyl phosphorous acid. As shown in FIG. 7, NTA and IDMPA represent two chelating ligands for lead that provide a high level of thermal endurance and remain chemically active to sulfide.

Figure 8:
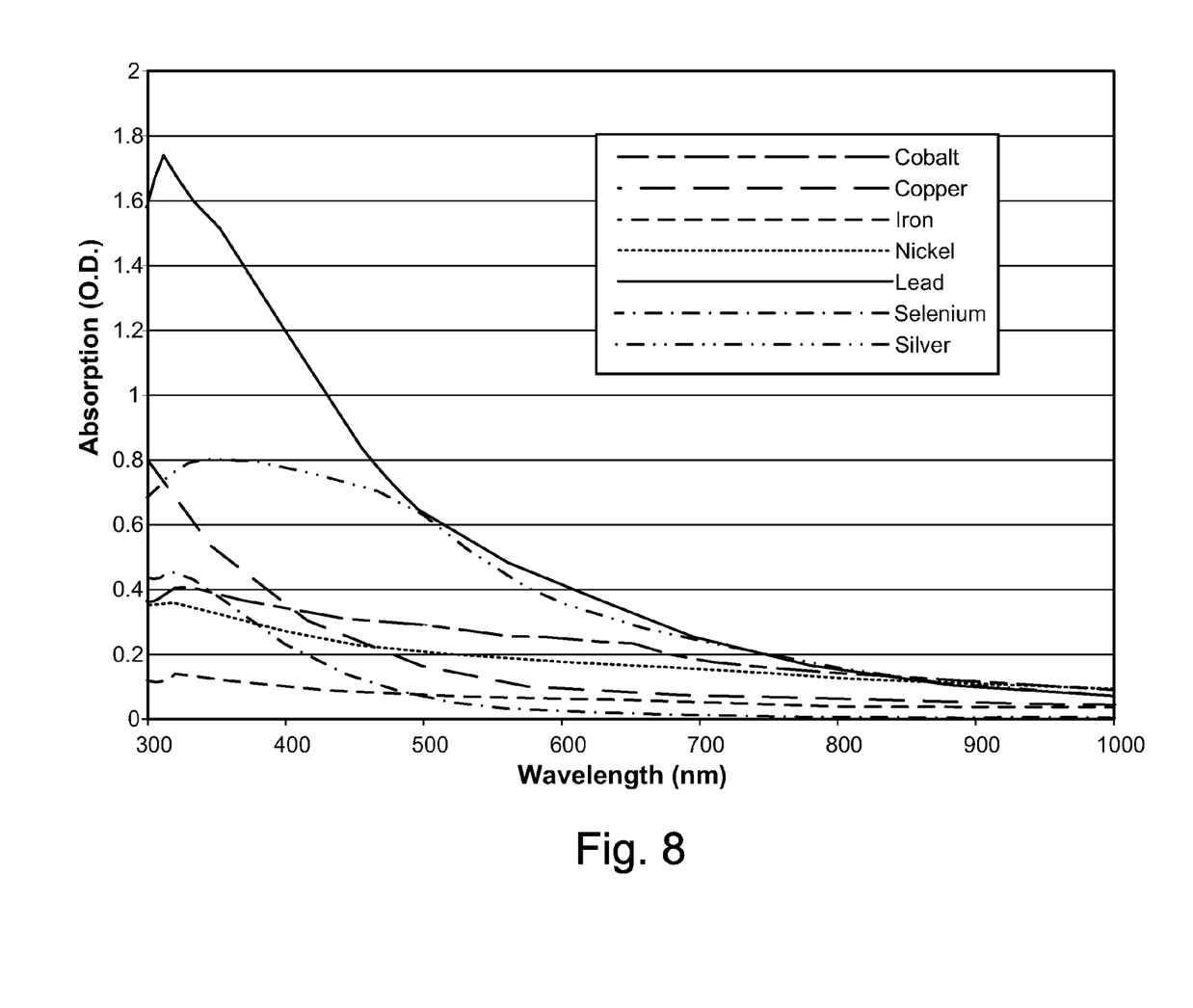
FIG. 8 shows optical absorption curves of various metal sulfides in Ludux®, according to embodiments of the invention.

FIG. 8 shows optical absorption curves of various metal sulfides in Ludux®, according to embodiments of the invention. Experiments in Ludox® solutions have shown that Nickel, Copper and Selenium can be used for in mixtures for detecting $H_2S$, in addition to Lead and Cadmium as described above. Copper and Selenium, in particular, give rise to a specific absorption peak which provides a clear distinction between absorbance due to the particles from scattering and absorbance due to oil or other components. Furthermore, other metals such as Cobalt, Silver and Tin could be useful in detection mixtures under some circumstances.

As has been described herein, the silica particles in Ludox® are dissolved in water. However, according to other embodiments of the invention, other solvents can be used with the detection mixtures. For example, the water can be replaced by formamide. This is done by the addition of formamide to the Ludox® and heating the solution to about 110 degrees C. The water will evaporate but the silica will remain suspended in the formamide. Formamide is an organic polar solvent. The silica suspension in formamide can be used with the detection mixtures as described herein. The formamide suspension offers some advantages over water. For example, formamide has a boiling point of 220 degrees C. which minimizes the risk of evaporation of the solvent. In the case of Ludox® the water will evaporate at 100 degrees C. causing the solution to gel, which could cause problems the tool when used downhole. Furthermore, the silica particles dissolved in formamide are insensitive to the salt concentration whereas the aqueous Ludox® mixture can tend to develop into a gel when in contact with higher concentrations salts. Higher loads of lead or other metal particles can be used with solvents such as formamide since such mixtures have less of tendency to gel. However, one disadvantage of silica particles in formamide can be a relatively rapid discoloring of the solution in formamide when exposed to sulfide. The coloring tends to disappear with time. Depending on the sulfide concentrations the color completely disappears within a few hours. According to other embodiments of the invention, other solvents can be used instead of water or formamide. When selecting an appropriate solvent, an organic solvent having relatively high polarity can be suitable, such as dimethylformamide, glycol.

Figure 9:
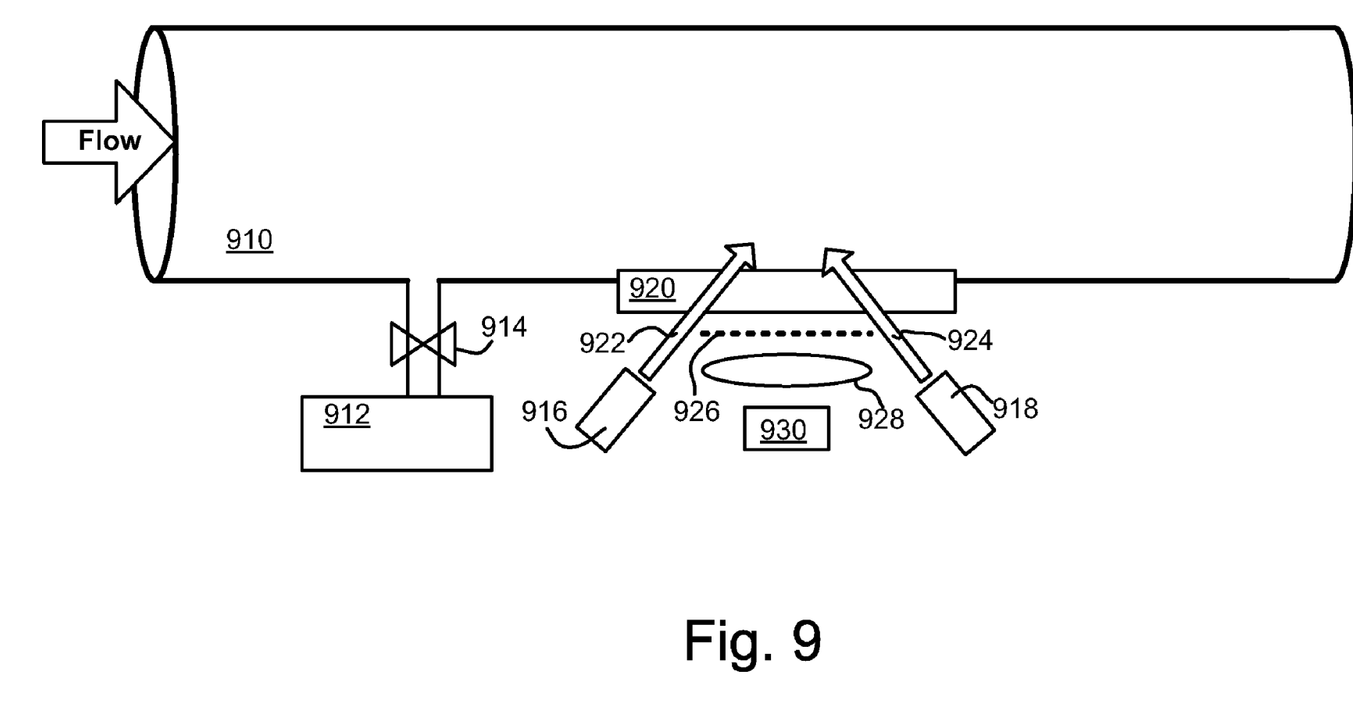
FIG. 9 shows an example of a flowline-based $H_2S$ detection system according to embodiments of the invention.

As mentioned, mixtures described according to the foregoing embodiments of the invention can be used in combination with a downhole optical detection system, such as Schlumberger's Live Fluid Analyser (LFA), which is operated as part of Schlumberger's openhole logging tool Modular Formation Dynamics Tester (MDT). FIG. 9 according to aspects of the invention, shows two examples of systems for optically detecting and measuring $H_2S$ downhole using the mixtures as described herein. FIG. 9 shows an example of a flowline-based $H_2S$ detection system according to embodiments of the invention. The flow line 910, carries test fluids from the formation, from the left side of flow line 910 in FIG. 9, to a borehole or to one or more sampling chambers, on the right side of flow line 910 in FIG. 9. The flow line 910 receives an amount of a suitable mixture from bottle 912. The flow of the mixture stored in bottle 912 into flow line 910 is controlled by an electromechanical valve 914. The mixture mixes with the fluids in the flow line 910 before reaching an interrogation window 920 down-stream. Window 920 is preferably made from a rugged material such as sapphire to withstand an aggressive flow within flow line 910. A light source 916 provides light 922 either in a broad spectrum of white light or at an appropriate wavelength (e.g. 815 nm, 680 nm or 570 nm, which is compatible with Schlumberger's LFA system in Schlumberger's MDT). Light 922 enters the flow line 910 via window 920 and illuminates the fluid in flow line 910. A suitable filter 926 and lens 928 aid in the detection of the signal from flow line 910 through window 920 by optical detector 930. Filter 926 is designed to only pass a narrow range of frequencies centered around the target wavelength (e.g. 815 nm, 680 nm or 570 nm). Relating to an aspect of the invention, in particular, absorption spectroscopy, detector 930 measures the optical density at the appropriate wavelength, which is then compared with a predefined calibration curve to establish the existence or determine the quantity of $H_2S$ in the formation fluid. The described operation is then repeated for every measurement. Alternatively, light source 918 can be used to provide light 924 into the flow line 910. Although FIG. 9 shows the window at one side of the flow line, according to a different embodiment of the invention, the measurement can be made with separated windows for illumination and detection, which can be located at opposite sides of the flow line 910.

Figure 10:
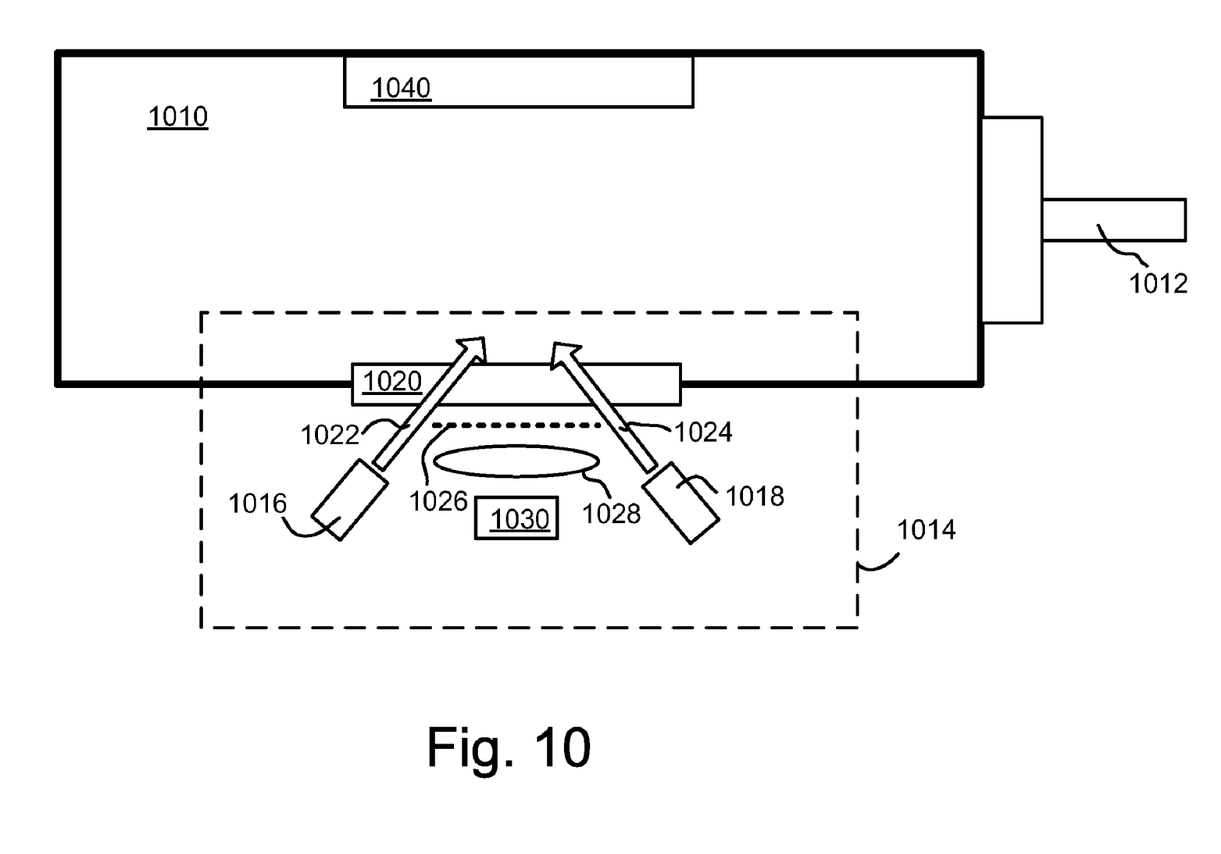
FIG. 10 shows an example of a sample bottle based $H_2S$ detection system according to embodiments of the invention.

FIG. 10 shows according to an aspect of the invention, an example of a sample bottle based $H_2S$ detection system. Sample bottle 1010 is housed in a downhole fluid sampling tool (not shown) such as Schlumberger's MDT. Prior to use, sample bottle 1010 is filled with the $H_2S$ detection mixture as described herein. During the sampling process downhole, the formation fluid is drawn into the sample bottle 1010 via inlet 1012 by creating an appropriate pressure gradient along the flow line. Formation fluid in a gas state is drawn or bubbled into the sample bottle 1010 thereby exposing the sampled formation fluid to the detection mixture in bottle 1010. Diffusion will act to mix the formation fluid with the detection mixture so as to generate a detectable signal. However, if according to an aspect of the invention, it is not practical to wait for sufficient diffusion to occur, such that a mixing system 1040 can be provided. Mixing system 1040 can be based on an acoustic transducer, such as described in U.S. Pat. No. 6,988,547, or in U.S. Pat. No. 6,758,090, both incorporated by reference herein. Optical detection system 1014 is provided on sample bottle 1010 which can be similar to the LFA system in Schlumberger's MDT tool. In particular, two light sources 1016 and 1018 provide light 1022 and 1024 respectively either in a broad spectrum of white light or at an appropriate wavelengths (e.g. 815 nm, 680 nm and 570 nm). The signal from sample bottle 1010 is detected by light detector 1030 via window 1020, preferably made of sapphire, filter 1026 and lens 1028. Filter 1026 is designed to only pass a narrow range of frequencies centered around the target wavelength (e.g. 815 nm, 680 nm or 570 nm). Detector 1030 measures the optical density at the appropriate wavelength, which is then compared with a predefined calibration curve to establish the existence or determine the quantity of $H_2S$ in the formation fluid.

Still referring to FIG. 10, and according to another embodiment of the invention, the sample bottle 1010 is filled with an $H_2S$ detection mixture, and the formation fluid is drawn into bottle 1010 as described above. However, the combined mixture and formation fluid is then pushed back out into a flow line such as flowline 910 in FIG. 9 where the optical interrogation can occur using a detection system as shown in FIG. 9. According to this embodiment of the invention, optical detection system 1014 need not be provided. Additionally, the mixing system 1040 can be used to sufficiently mix the detection mixture and the formation fluid. If sufficient mixing occurs by the drawing in and pushing out process of the formation fluid, as well as diffusion in bottle 1010 and flowline 910, then mixing system 1040 need not be used.

Referring to FIGS. 9 and 10, and according to another embodiment of the invention, show that fluorescence spectroscopy can be used to detect the reacted metal sulfide species in flowline 910 of FIG. 9 or bottle 1010 of FIG. 10. Since many metal sulfide species exhibit strong fluorescence, one or more of the light sources 916, 918, 1016 and 1018 can be used as an excitation energy source, and the florescence from the metal sulfide species can be detected using filters and detectors 926, 1026 and 930, 1030 respectively. Existing downhole fluorescence detection technology can be used such as used in the Composition Fluid Analyzer module to MDT tester suite provided by Schlumberger. Fluorescence spectroscopy can be especially useful when the concentrations of metal sulfide are relatively high, due to an increased fluorescence signal relative to background noise.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, although the target substance in the embodiments described has been $H_2S$, it has been found that some thiols such as $CH_3SH$, $C_2H_5SH$ and $C_3H_7SH$ can also be detected using the embodiments described herein. In another example, although silica based nanoparticles have been described in the embodiments herein, alternative materials such alumina ($Al_2O_3$), titania ($TiO_2$), cerium oxide ($CeO_2$) or other metal oxides can be use for the nanoparticle material. In another example, uncharged metal particles can be used instead of ions. Specifically, elemental metal particles can be manufactured or purchased having a size domain of 5-200 nm and zero surface charge.

Further, while the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system for detecting hydrogen sulfide downhole, the system comprising:
   a detection mixture including:
   1) nanoparticles having discrete uniform spheres with a negatively charged silica particle surface that repel one another thereby yielding a stable solution, wherein the ratio of nanoparticles to water by weight is between about 25% and about 45%, and
   2) metal ions having positively charged metal species for reacting with hydrogen sulfide thereby forming a metal sulfide species;
   wherein dispersing the metal sulfide species into the nanoparticles selectively stabilizes the detection mixture, wherein stabilizing the detection mixer is achieved by electrostatic charge matching between the metal sulfide species and the nanoparticles, resulting in the stabilized detection mixer being a stable homogeneous colloidal liquid detection mixer;
   a downhole mixture delivery system for exposing the detection mixture to fluids collected from a subterranean formation in a downhole setting; and
   an optical detection system for detecting the reacted mixture that indicated the presence of hydrogen sulfide in the exposed formation fluid.

2. The system according to claim 1, wherein the metal ions for reacting with hydrogen sulfide form a metal sulfide, and nanoparticles are sized so as to inhibit significant aggregation of the metal sulfide so as to enable spectroscopic detection of the metal sulfide downhole.

3. The system according to claim 2, wherein the metal ions are ions from one or more metals selected from the group consisting of Lead, Copper, Selenium, Nickel, Cadmium, and Tin, and the mixture is a colloidal mixture in an aqueous solution.

4. The system according to claim 2, wherein the nanoparticles are sized between about 7 nm and about 25 nm, and the detection mixture further includes chelating ligands for sustaining thermal endurance of the mixture under downhole conditions.

5. The system according to claim 1, wherein the mixture delivery system includes a mixture reservoir and a valve system for introducing the mixture into a flowline for carrying the subterranean fluids, and the optical detection system includes a light source, an interrogation window in the flowline and an optical detector.

6. The system according to claim 1, wherein the mixture delivery system includes a sample bottle for containing the detection mixture and a fluid delivery system for introducing the subterranean fluids into the sample bottle, and the optical detection system includes a light source, an interrogation window and an optical detector.

7. The system according to claim 1, wherein the optical detection system uses fluorescence spectroscopy, and wherein the metal ions for reacting with hydrogen sulfide form a metal sulfide, and nanoparticles are sized so as to inhibit significant aggregation of the metal sulfide so as to enable spectroscopic detection of the metal sulfide downhole.

* * * * *